(12) United States Patent
Smith et al.

(10) Patent No.: US 8,247,461 B2
(45) Date of Patent: Aug. 21, 2012

(54) OPHTHALMIC AND CONTACT LENS SOLUTION

(76) Inventors: Francis X. Smith, Salem, NH (US); John Randall Tracey, Salem, NH (US)

( * ) Notice: Subject to any disclaimer, the term of this patent is extended or adjusted under 35 U.S.C. 154(b) by 0 days.

(21) Appl. No.: 12/693,878

(22) Filed: Jan. 26, 2010

(65) Prior Publication Data

US 2010/0122918 A1    May 20, 2010

Related U.S. Application Data

(63) Continuation of application No. 10/842,162, filed on May 10, 2004, now Pat. No. 7,678,836, which is a continuation of application No. 09/706,338, filed on Nov. 4, 2000, now abandoned.

(60) Provisional application No. 60/163,455, filed on Nov. 4, 1999.

(51) Int. Cl.
*A61K 31/74* (2006.01)
*A61K 47/00* (2006.01)
*B01D 12/00* (2006.01)

(52) U.S. Cl. .................... 516/204; 134/901; 424/78.04; 510/112; 514/786; 514/839

(58) Field of Classification Search .................. 516/204; 134/901; 424/78.04; 510/112; 514/786, 514/839
See application file for complete search history.

(56) References Cited

U.S. PATENT DOCUMENTS

| | | | |
|---|---|---|---|
| 1,432,345 | A | 10/1922 | Lasker |
| 2,976,576 | A | 3/1961 | Wichterle et al. |
| 3,428,576 | A | 2/1969 | Dickinson et al. |
| 3,429,576 | A | 2/1969 | Yoshiaki Ikeda |
| 3,503,393 | A | 3/1970 | Manley |
| 3,591,329 | A | 7/1971 | Chromecek et al. |
| 3,689,673 | A | 9/1972 | Phares, Jr. |
| 3,755,561 | A | 8/1973 | Rankin |
| 3,873,696 | A | 3/1975 | Randeri et al. |
| 3,876,768 | A | 4/1975 | Blank |
| 3,888,782 | A | 6/1975 | Boghosian et al. |
| 3,910,296 | A | 10/1975 | Karageozian et al. |
| 3,911,107 | A | 10/1975 | Krezanoski |
| 3,912,450 | A | 10/1975 | Boucher |
| 3,943,251 | A | 3/1976 | Medow et al. |
| 4,022,834 | A | 5/1977 | Gundersen |
| 4,029,817 | A | 6/1977 | Blanco et al. |
| 4,046,706 | A | 9/1977 | Krezanoski |
| 4,136,173 | A | 1/1979 | Pramoda et al. |
| 4,136,175 | A | 1/1979 | Rideout et al. |
| 4,136,534 | A | 1/1979 | Villa |
| 4,209,817 | A | 6/1980 | McGinnis |
| 4,354,952 | A | 10/1982 | Riedhammer et al. |
| 4,361,458 | A | 11/1982 | Grajek et al. |
| 4,361,548 | A | 11/1982 | Smith et al. |
| 4,361,549 | A | 11/1982 | Kung et al. |
| 4,394,381 | A | 7/1983 | Sherrill |
| 4,439,417 | A * | 3/1984 | Matsunaga et al. ........... 510/127 |
| 4,525,346 | A | 6/1985 | Stark |
| 4,599,360 | A | 7/1986 | Fukami et al. |
| RE32,672 | E | 5/1988 | Huth et al. |
| 4,748,189 | A * | 5/1988 | Su et al. .................... 514/781 |
| 4,758,595 | A | 7/1988 | Ogunbiyi et al. |
| 4,783,488 | A | 11/1988 | Ogunbiyi et al. |
| 4,820,352 | A | 4/1989 | Riedhammer et al. |
| 4,826,879 | A | 5/1989 | Yamamoto et al. |
| 4,836,986 | A | 6/1989 | Ogunbiyi et al. |
| 4,863,900 | A | 9/1989 | Pollock et al. |
| 4,891,423 | A | 1/1990 | Stockel |
| 4,894,454 | A | 1/1990 | Paradies |
| 4,988,710 | A * | 1/1991 | Olney ....................... 514/318 |
| 4,997,626 | A | 3/1991 | Dziabo et al. |
| 5,030,721 | A * | 7/1991 | Kasai et al. ................. 536/41 |
| 5,089,261 | A * | 2/1992 | Nitecki et al. ............. 424/85.2 |
| 5,122,354 | A | 6/1992 | Tsuji et al. |
| 5,174,872 | A * | 12/1992 | Scott ....................... 205/779 |
| 5,175,161 | A | 12/1992 | Yokoyama et al. |
| 5,182,258 | A | 1/1993 | Chiou |
| 5,192,535 | A | 3/1993 | Davis et al. |
| 5,279,673 | A | 1/1994 | Dziabo et al. |
| 5,300,296 | A | 4/1994 | Holly et al. |
| 5,306,440 | A | 4/1994 | Ripley et al. |
| 5,380,303 | A | 1/1995 | Holly et al. |
| 5,401,327 | A | 3/1995 | Ellis et al. |
| 5,422,073 | A | 6/1995 | Mowrey-McKee et al. |
| 5,439,572 | A | 8/1995 | Pankow |
| 5,449,658 | A | 9/1995 | Unhoch et al. |
| 5,494,937 | A | 2/1996 | Asgharian et al. |
| 5,547,990 | A | 8/1996 | Hall et al. |
| 5,591,773 | A | 1/1997 | Gronberger et al. |
| 5,607,681 | A | 3/1997 | Galley et al. |

(Continued)

FOREIGN PATENT DOCUMENTS

EP        0812592        12/1997

(Continued)

OTHER PUBLICATIONS

Search Report for EP 0199961.*
Ballweber et al., "In Vitro Microbicidal Activities of Cecropin Peptides D2A21 and D4E1 and Gel Formulations Containing 0.1 to 2% D2A21 against Chlamydia Trachomatis", Antimicrobial Agents and Chemotherapy, Jan. 2002, pp. 34-41, vol. 46, No. 1.
Delucca et al., "Fungicidal Properties, sterol binding, and proteolytic resistance of the synthetic peptide D4E1", Canadian Journal of Microbiology, Jun. 1998, pp. 514-520, vol. 44, No. 6.
Keay, L., Moser, P.W. and Wildo, B.S., "Proteases of the Genus Bacillus II. Alkaline Proteases", Biotechnology & Bioengineering, Mar. 1970, pp. 213-249, vol. XII.
Keay, L., and Moser, P.W., "Differentiation of Alkaline Proteases from Bacillus Species", Biochemical and Biophysical Research Communications, 1969, pp. 600-604, vol. 34, No. 5.
Schutte, L., et al., "The Substitution Reaction of Histidine and Some Other Imidazole Derivatives With Iodine", Tetrahedron, Supplement No. 7, 1965, pp. 295-306.

*Primary Examiner* — Timothy J. Kugel

(74) *Attorney, Agent, or Firm* — Hiscock & Barclay, LLP

(57) ABSTRACT

An ophthalmic solution comprising a polyethoxylated glyceride in the range of 0.001 to about 10 percent by weight and a buffer agent. These solutions impart surprising comfort and wearability to contact lenses. At the same time the solutions provide good preservative capacity and do not increase protein deposit.

7 Claims, No Drawings

U.S. PATENT DOCUMENTS

| | | | |
|---|---|---|---|
| 5,624,958 A | 4/1997 | Isaacs et al. | |
| 5,631,287 A * | 5/1997 | Schneider | 514/530 |
| 5,660,862 A | 8/1997 | Park et al. | |
| 5,661,130 A | 8/1997 | Meezan et al. | |
| 5,674,450 A | 10/1997 | Lin et al. | |
| 5,691,379 A | 11/1997 | Ulrich et al. | |
| 5,718,895 A | 2/1998 | Asgharian et al. | |
| 5,719,110 A | 2/1998 | Cook | |
| 5,741,817 A | 4/1998 | Chowhan et al. | |
| 5,770,582 A | 6/1998 | von Borstel et al. | |
| 5,780,450 A | 7/1998 | Shade | |
| 5,807,585 A | 9/1998 | Martin et al. | |
| 5,811,446 A | 9/1998 | Thomas | |
| 5,854,303 A | 12/1998 | Powell et al. | |
| 5,869,468 A | 2/1999 | Freeman | |
| 5,888,950 A | 3/1999 | Potini et al. | |
| 5,891,733 A | 4/1999 | Inove | |
| 5,925,317 A | 7/1999 | Rogalskyj et al. | |
| 5,925,371 A | 7/1999 | Ishiwatari | |
| 5,942,218 A | 8/1999 | Kirschner et al. | |
| 5,945,446 A | 8/1999 | Laub | |
| 5,952,320 A | 9/1999 | Davidsen et al. | |
| 5,965,736 A * | 10/1999 | Akhavan-Tafti | 548/110 |
| 5,968,904 A | 10/1999 | Julian et al. | |
| 6,001,805 A | 12/1999 | Jaynes et al. | |
| 6,008,195 A | 12/1999 | Selsted | |
| 6,022,732 A | 2/2000 | Bakhit et al. | |
| 6,056,920 A * | 5/2000 | Lepre | 422/61 |
| 6,117,869 A | 9/2000 | Picard et al. | |
| 6,121,327 A | 9/2000 | Tsuzuki et al. | |
| 6,126,706 A * | 10/2000 | Matsumoto et al. | 134/34 |
| 6,139,646 A | 10/2000 | Asgharian et al. | |
| 6,153,568 A | 11/2000 | McCanna et al. | |
| 6,162,398 A | 12/2000 | Shuler | |
| 6,191,110 B1 | 2/2001 | Jaynes et al. | |
| 6,309,596 B1 | 10/2001 | Xia et al. | |
| 6,309,658 B1 | 10/2001 | Xia et al. | |
| 6,432,893 B1 | 8/2002 | Doi et al. | |
| 6,617,291 B1 | 9/2003 | Smith | |
| 6,624,203 B1 | 9/2003 | Smith | |
| 2003/0190258 A1 | 10/2003 | Smith | |
| 2005/0042198 A1 * | 2/2005 | Smith et al. | 424/78.38 |

FOREIGN PATENT DOCUMENTS

| | | | |
|---|---|---|---|
| EP | 0923950 A3 | 12/2000 | |
| GB | 1398058 | 3/1973 | |
| JP | 58040517 A | 1/1983 | |
| JP | 10108899 | 4/1998 | |
| JP | 2000016965 A | 1/2000 | |
| RU | 2127100 | 3/1999 | |
| RU | 2127106 C1 * | 3/1999 | |
| WO | WO9101763 | 2/1991 | |
| WO | WO 92/04905 A1 * | 4/1992 | |
| WO | WO9211876 | 4/1992 | |
| WO | WO9221049 | 11/1992 | |
| WO | WO9400160 | 1/1994 | |
| WO | WO9415649 A1 | 7/1994 | |
| WO | WO 9415649 A1 * | 7/1994 | |
| WO | WO9500176 | 1/1995 | |
| WO | WO9606603 | 3/1996 | |
| WO | WO9730834 | 9/1997 | |
| WO | WO9741215 | 11/1997 | |
| WO | WO9923887 | 5/1999 | |
| WO | WO9937295 | 7/1999 | |
| WO | WO0007634 A | 2/2000 | |
| WO | WO0012514 | 3/2000 | |

* cited by examiner

OPHTHALMIC AND CONTACT LENS SOLUTION

CROSS-REFERENCE TO RELATED APPLICATIONS

This application is a continuation of and claims priority from U.S. patent application Ser. No. 10/842,162, filed May 10, 2004, now U.S. Pat. No. 7,678,836 which is a continuation of U.S. patent application Ser. No. 09/706,338 filed Nov. 4, 2000 now abandoned which claims priority from U.S. Provisional Application Ser. No. 60/163,455 filed Nov. 4, 1999. The contents of which are incorporated in their entirety by reference.

BACKGROUND

The present invention relates to novel ophthalmic solutions that contain a ethoxylated glyceride as an additive to improve the wettability and to decrease the degree of protein and polymeric preservative binding to contact lens surfaces. These compositions may also comprise other agents in contact lens and ophthalmic solutions such as buffers, tonicity agents, wetting agents, enzymes, hydrogen peroxide, demulcents, thickeners, sequestering agents (chelating agents), surface active agents and preservative agents. The ethoxylated glycerides are particularly useful in contact lens treatment solutions, contact lens wetting solutions, solutions used to store contact lenses and solutions used to clean or rinse contact lenses. It has been found that surprisingly the addition of ethoxylated glycerides improve the comfort of lenses treated with such solution and that this increased comfort is surprisingly long-lasting in its effect. The ethoxylated glycerides maybe mono-, di- or triglycerides;

DETAILED DESCRIPTION

The solutions of the present invention are made by one of two methods. First the ethoxylated glyceride may be melted and added to an aqueous solution which includes the other agents to be used in the desired formulation, or the additional agents may be added prior to the addition of the melted ethoxylated glyceride. Second, the ethoxylated glyceride may be dissolved in an alcohol base and this liquid mixture, added to the aqueous base. Ethoxylated glycerides are commercially available from numerous commercial sources and include Polyoxyl 40 hydrogenated castor oil (Cremophor RH 40), polyoxyl 60 hydrogenated castor oil (Cremophor RH 60), PEG-30 Castor Oil (Incrocas 30), PEG-35 Castor Oil (Cremophor EL, Incrocas 35), or PEG-40 Castor Oil (Cremophor EL, Incrocas), Cremophor EL®, Emulphor EL®, glycerol polyethyleneglycol riciinoleate, gycerol polyethyleneglycol oxystearate, polyethoxylated hydrogenated castor oil, or polyethoxylated vegetable oil. The ethoxylated glycerides useful in the present invention may include surfactants sold as PEG-6 Caprylic/Capric Glycerides PEG-8 Caprylic/Capric Glycerides; PEG-2 Castor Oil; PEG-3 Castor Oil; PEG-4 Castor Oil; PEG-5 Castor Oil; PEG-8 Castor Oil; PEG-9 Castor Oil; PEG-10 Castor Oil; PEG-11 Castor Oil; PEG-15 Castor Oil; PEG-20 Castor Oil; PEG-25 Castor Oil; PEG-30 Castor Oil; PEG-33 Castor Oil; PEG-35 Castor Oil; PEG-36 Castor Oil; PEG-40 Castor Oil; PEG-50 Castor Oil; PEG-54 Castor Oil; PEG-55 Castor Oil; PEG-60 Castor Oil; PEG-100 Castor Oil; PEG-200 Castor Oil; PEG-18 Castor Oil Dioleate; PEG-60 Corn Glycerides; PEG-20 Evening Primrose Glycerides; PEG-60 Evening Primrose Glycerides; PEG-7 Glyceryl Cocoate; PEG-30 Glyceryl Cocoate; PEG-78 Glyceryl Cocoate; PEG-80 Glyceryl Cocoate; PEG-12 Glyceryl Dioleate; PEG-15 Glyceryl Isostearate; PEG-20 Glyceryl Isostearate; PEG-30 Glyceryl Isostearate; PEG-60 Glyceryl Isostearate; PEG-12 Glyceryl Laurate; PEG-20 Glyceryl Laurate; PEG-23 Glyceryl Laurate; PEG-30 Glyceryl Laurate; PEG-10 Glyceryl Oleate; PEG-15 Glyceryl Oleate; PEG-30 Glyceryl Oleate; PEG-20 Glyceryl Ricinoleate; PEG-5 Glyceryl Sesquioleate; PEG-S Glyceryl Stearate; PEG-10 Glyceryl Stearate; PEG-25 Glyceryl Stearate; PEG-30 Glyceryl Stearate; PEG-120 Glyceryl Stearate; PEG-200 Glyceryl Stearate; PEG-28 Glyceryl Tallowate; PEG-80 Glyceryl Tallowate; PEG-200 Glyceryl Tallowate; PEG-S Glyceryl Triisostearate; PEG-5 Hydrogenated Castor Oil; PEG-7 Hydrogenated Castor Oil; PEG-16 Hydrogenated Castor Oil; PEG-20 Hydrogenated Castor Oil; PEG-25 Hydrogenate Castor Oil; PEG-30 Hydrogenate Castor Oil; PEG-35 Hydrogenate Castor Oil; PEG-40 Hydrogenate Castor Oil; PEG-45 Hydrogenate Castor Oil; PEG-50 Hydrogenate Castor Oil; PEG-54 Hydrogenate Castor Oil; PEG-55 Hydrogenate Castor Oil; PEG-60 Hydrogenate Castor Oil; PEG-80 Hydrogenate Castor Oil; PEG-100 Hydrogenate Castor Oil; PEG-200 Hydrogenate Castor Oil; PEG-40 Hydrogenated Castor Oil PCA Isostearate; PEG-5 Hydrogenated Corn Glycerides; and PEG-8 Hydrogenated Fish Glycerides; which are all available from known commercial sources The solutions of the present invention may contain other additives including but not limited to buffers, tonicity agents, demulcents, wetting agents, preservatives, sequestering agents (chelating agents), surface active agents, and enzymes.

Other aspects of the claimed solutions include adding to the solution from 0.001 to 1 weight percent chelating agent (preferably disodium EDTA) and/or additional microbicide, (preferably 0.00001 to 0.1 or 0.00001 to 0.01) weight percent polyhexamethylene biquanide (PHMBO, N-alkyl-2-pyrrolidone, chlorhexidine, polyquatemium-1, hexetidine, bronopol, alexidine, low concentrations of hydrogen peroxide, and ophthalmologically acceptable salts thereof Ophthalmologically acceptable chelating agents useful in the present invention include amino carboxylic acid compounds or water-soluble salts thereof, including ethylenediaminetetraacetic acid, nitrilotriacetic acid, diethylenetriamine pentaacetic acid, hydroxyethylethylenediaminetriacetic acid, 1,2-diaminocyclohexanetetraacetic acid, ethylene glycol bis(beta-aminoethyi ether) in N,N,N',N' tetraacetic acid (EGTA), aminodiacetic acid and hydroxyethylamino diacetic acid. These acids can be used in the form of their water soluble salts, particularly their alkali metal salts. Especially preferred chelating agents are the di-, tri- and tetra-sodium salts of ethylenediaminetetraacetic acid (EDTA), most preferably disodium EDTA (Disodium Edetate).

Other chelating agents such as citrates and polyphosphates can also be used in the present invention. The citrates which can be used in the present invention include citric acid and its mono-, di-, and tri-alkaline metal salts. The polyphosphates which can be used include pyrophosphates, triphosphates, tetraphosphates, trimetaphosphates, tetrametaphosphates, as well as more highly condensed phosphates in the form of the neutral or acidic alkali metal salts such as the sodium and potassium salts as well as the ammonium salt.

The pH of the solutions should be adjusted to be compatible with the eye and the contact lens, such as between 6.0 to 8.0, preferably between 6.8 to 7.8 or between 7.0 to 7.6. Significant deviations from neutral (pH 7.3) will cause changes in the physical parameters (i.e. diameter) in some contact lenses. Low pH (pH less than 5.5) can cause burning and stinging of the eyes, while very low or very high pH (less than 3.0 or greater than 10) can cause ocular damage.

The additional preservatives employed in the present invention are known, such as polyhexamethylene biguanide, N-alkyl-2-pyrrolidone, chlorhexidine, polyhexamethylenebiguanide, alexidine, polyquatemium-1, hexetidine, bronopol and a very low concentration of hydrogen peroxide, e.g., 30 to 200 rpm.

The solutions of the invention are compatible with both rigid gas permeable and hydrophilic contact lenses during storage, cleaning, wetting, soaking, rinsing and disinfection.

A typical aqueous solution of the present invention may contain additional ingredients which would not affect the basic and novel characteristics of the active ingredients described earlier, such as tonicity agents, surfactants and viscosity inducing agents, which may aid in either the lens cleaning or in providing lubrication to the eye. Suitable tonicity agents include sodium chloride, potassium chloride, glycerol or mixtures thereof. The tonicity of the solution is typically adjusted to approximately 240-310 milliosmoles per kilogram solution (mOsm/kg) to render the solution compatible with ocular tissue and with hydrophilic contact lenses. In one embodiment, the solution contains 0.01 to 0.5 weight percent sodium chloride.

Suitable viscosity inducing agents can include lecithin or the cellulose derivatives such as hydroxyrnethylcellulose, hydroxypropylcellulose and methylcellulose in amounts similar to those for surfactants, above.

EXAMPLE 1

Hydrophilic contact lenses were placed flat onto glass slides and rinsed with water to remove any debris. These slides were placed in a petri dish and covered with a few drops of each of the test solutions previously prepared in either water, an aqueous isotonic sodium chloride solution, or an aqueous phosphate buffered solution made isotonic with sodium chloride and adjusted to pH 7.3. Each petri plate was covered and placed in a refrigerator overnight. The following day, the slides were removed and allowed to equilibrate to room temperature. The lenses were rinsed with water and the excess water was removed. One 5 uL drop of mineral oil stained with Oil Red O was placed onto one lens for each solution. After ten minutes, the lenses were observed for the ability of the oil drop to spread.

| Additive | Solution Matrix | Oil Dispersibility | Water Dispersibility |
|---|---|---|---|
| 1% polyoxyl 40 hydrogenated castor oil (Cremophor RH 40) | water | 4 | 5 |
| 1% polyoxyl 40 hydrogenated castor oil (Cremophor RH 40) | buffer water | 5 | 5 |
| 1% polyoxyl 40 hydrogenated castor oil (Cremophor RH 40) | sodium choride water | 2 | 5 |
| 1% polyoxyl 40 hydrogenated castor oil (Cremophor RH 40) | buffer sodium chloride water | 3 | 5 |
| 1% Polysorbate 80 (Tween 80) | sodium choride water | 4 | 5 |
| 1% Poloxamine 1107 (Tetronic 1107) | sodium choride water | 2 | 5 |
| 1% Poloxamer 407 (Pluronic F127) | sodium choride water | 2 | 5 |
| 1% Polysorbate 80 (Tween 80) | buffer sodium chloride water | 3 | 5 |
| 1% Poloxamine 1107 (Tetronic 1107) | buffer sodium chloride water | 1 | 5 |
| 1% Poloxamer 407 (Pluronic F127) | buffer sodium chloride water | 1 | 5 |
| Water | water | 1 | 5 |

Key
1 non-spreading drop
2 poor spreading drop
3 moderate spreading drop
4 increased spreading drop
5 thin spreading film The results demonstrates that exposure of the contact lens to the ethoxylated glyceride will generate a durable modified surface capable of allow the formation of a thin oil and aqueous film. This characteristic mimics mucin and is essential for the proper tear layer formation of over the lens. A score of 3 or better is considered acceptable. This experiment also illustrates the synergistic improvement when the ethoxylated glyceride is exposed in the presence of a buffer. The inability of the Poloxamer and Poloxamine to allow the oil film to spread across the lens demonstrates that not all surface active agents will promote the spreading of a properly formed tear film over the contact lens, surface.

EXAMPLE 2

Example of Protein Deposition Inhibition

Contact lenses were soaked and heated in test solutions to which a radio-labeled lysozyme was present in a known amount for a period of 12 hours at 37 degrees Celsius. The lenses were rinsed with distilled water in order to remove residual solution. The lenses were then assayed for protein deposition using a Beckman BioGamma 1 counter. Results were reported in ug/lens.

|  | Lens A ug/lens | Lens B ug/lens | Average ug/lens |
|---|---|---|---|
| Phosphate buffer control | 1,043 | 865 | 954 |
| Cremophor RH40 (1%) In Phosphate Buffer | 15 | 23 | 19 |

Ethoxylated Castor Oil was a 1 percent w/v solution. The matrix control was phosphate buffer and sodium chloride. The polyoxyl 40 hydrogenated castor oil solution had lower protein binding than the control.

EXAMPLE 3

Example of Protein Deposition Inhibition

Isotonic aqueous phosphate buffered solutions were prepared and adjusted to pH 7.4. Contact lenses were soaked in 25 mL of the test solutions overnight. Afterwards, lysozyme was added to the tubes and warmed to 37 degrees Celsius for 12 hours. The lenses were rinsed with distilled water in order to remove residual solution. The lenses were assayed for protein deposition by the RCA method and detected on an HP PDA Spectrophotometer. Results were reported in ug/lens.

| Solution | ug lysozyme per lens |
|---|---|
| Marketed Product Control (phosphate buffer, Poloxamer) | >18.3 |
| Phosphate buffer control | >26.16 |
| Cremophor RH40 (1%) In Phosphate Buffer | 9.78 |

Ethoxylated Castor Oil was a 1 percent w/v solution. The matrix control was phosphate buffer and sodium chloride. The polyoxyl 40 hydrogenated castor oil solution had lower protein binding than the control.

EXAMPLE 4

An example of a preferred disinfecting formulation of the subject invention is provided below in Table 1. This solution is prepared by weighing out the necessary amount of the tricine, creatine, choline chloride, sodium chloride and edetate disodium into a vessel containing approximately 90% of the water volume. After each of the ingredients has dissolved, the pH is adjusted to 7.3 with either 1 N sodium hydroxide or 1 N hydrochloric acid. Following this, the polyhexamethylene biguanide is added and the solution is brought to final volume with purified water. The final product has the composition shown in the Table below.

| Constituent | | Weight/Volume |
|---|---|---|
| Polyhexamethylene-biguanide HC1 | 20% w/w solution available under the mark Cosmocil CQ, from Avecia | 0.0001% |
| Tricine | Spectrum | 1.0% |
| Creatine | Spectrum | 0.25% |
| Choline Chloride | Amersco | 0.5% |
| Edetate Disodium | Spectrum | 0.055% |
| Polyoxyl 40 Hydrogenated Castor Oil | Cremophor RH 40 from BASF Co. | 0.1% |
| Sodium Chloride | Fisher Scientific | As required for tonicity adjustment 300 mOsm |
| Hydrochloride Acid, 1N | VWR | as required for pH adjustment to 7.3 |
| Sodium Hydroxide, 1N | Mallinckrodt | as required for pH adjustment to 7.3 |
| Purified Water | | Balance to 100% |

This solution may be used to rinse, clean, and store contact lenses on a daily basis.

EXAMPLE 5

An example of a preferred formulation for a contact lens vial storage of the subject invention is provided below in Table I. This solution is prepared by weighing out the necessary amount of the sodium borate, boric acid, and sodium chloride into a vessel containing approximately 90% of the water volume. After each of the ingredients has dissolved, the pH is adjusted to 7.3 with either 1 N sodium hydroxide or 1 N hydrochloric acid. The final product had the composition shown in Table I below.

| Constituent | | Weight/Volume |
|---|---|---|
| Sodium Borate | Spectrum | 1.0% |
| Boric Acid | Spectrum | 0.25% |
| Polyoxyl 40 Hydrogenated Castor Oil | Cremophor RH40 from BASF | 0.1% |
| Sodium Chloride | Fisher Scientific | As required for tonicity adjustment 300 mOsm |
| Hydrochloride Acid, 1N | VWR | as required for pH adjustment to 7.3 |
| Sodium Hydroxide, 1N | Mallinckrodt | as required for pH adjustment to 7.3 |
| Purified Water | | Balance to 100% |

EXAMPLE 6

The following are useful disinfecting solutions within the scope of the present invention that may be used for all purpose disinfecting solutions. They are made according to generally acceptable procedures except that the ethoxylated glycerides must be first be dissolved in warm water prior to the addition of the other components.

| Constituent | Supplier | % Weight/Volume | Amount |
|---|---|---|---|
| Purified Water | | to 80% | 40 mL |
| Tricine | Spectrum | 1.0% | 0.500 g |
| Carnitine | Spectrum | .25% | 0.125 g |
| Betaine HCl | Spectrum | 0.1% | 0.050 g |
| Choline Chloride | Amresco | 0.5% | 0.250 g |
| Inositol | Spectrum | 0.1% | 0.050 g |
| Edetate Disodium | Spectrum | 0.055% | 0.0275 g |
| Polyoxyl 40 Hyrdogenated Castor Oil | Cremophor RH 40 from BASF Co. | 0.1% | 0.5 mL of 10% |
| Hydrochloride Acid, 1N | | As required for pH adjustment to 7.3 | As required for pH adjustment to 7.3 |
| Sodium Hydroxide, 1N | | As required for pH adjustment to 7.3 | As required for pH adjustment to 7.3 |
| Purified Water | | To 98% | Dilute to 49 mL |

-continued

| Constituent | Supplier | % Weight/Volume | Amount |
|---|---|---|---|
| Sodium Chloride | Fisher | As required for tonicity adjustment 300 mOsm | As required for tonicity adjustment 300 mOsm |
| Polyhexamethylene-biguanide HCl | 20% w/w solution available under the mark Cosmocil CQ from Avecia | 0.0001% | 50 uL of 0.1% |
| Purified Water | | Balance to 100% | Dilute to 50 mL |

EXAMPLE 7

The following are formulations within the scope of the invention of formulations intended to be used as lens-vial solutions that are used to store lenses prior to their use. These solutions have the effect of treating the contact lens in the solution and rendering the lens more comfortable in use.

| Constituent | Supplier | % Weight/Volume | Amount |
|---|---|---|---|
| Purified Water | | To 80% | 40 mL |
| Tricine | Spectrum | 1.0% | 0.500 g |
| Carnitine | Spectrum | 0.25% | 0.125 g |
| Inositol | Spectrum | 0.1% | 0.050 g |
| Hydrochloride Acid, 1N | | As required for pH adjustment to 7.3% | As required for pH adjustment to 7.3% |
| Sodium Hydroxide, 1N | | As required for pH adjustment to 7.3% | As required for pH adjustment to 7.3% |
| Polyoxyl 40 Hydrogenated Castor Oil | Cremophor RH 40 from BASF Co. | 0.1% | 0.5 mL of 10% |
| Purified Water | | To 98% | Dilute to 49 mL |
| Sodium Chloride | Fisher | As required for tonicity adjustment 300 mOsm | As required for tonicity adjustment 300 mOsm |
| Purified Water | | Too 100% | Dilute to 50 mL |

What is claimed is:

1. An ophthalmic contact lens solution comprising: 0.001 to 10 percent by weight ethoxylated glyceride; 0.001 to 2 weight percent of a physiologically acceptable buffer adjusted so the pH of solution is between 6.5 and 7.8, 0.00001 to 0.1 weight percent of a polymeric preservative and the balance water.

2. The solution of claim 1 which further comprises 0.01 to 2 weight percent of a physiologically acceptable tonicity agent adjusted so the solution is isotonic between 240 and 310 mOsm/kg.

3. The solution of claim 1 wherein the ethoxylated glyceride is chosen from the group of compounds consisting of Polyoxyl 40 hydrogenated castor oil, polyoxyl 60 hydrogenated castor oil, PEG-30 Castor Oil, PEG-35 Castor Oil, or PEG-40 Castor Oil, glycerol polyethyleneglycol riciinoleate, gycerol polyethyleneglycol oxystearate, polyethoxylated hydrogenated castor oil, or polyethoxylated vegetable oil.

4. The solution of claim 1 wherein the buffer is selected from the group consisting of organic amines, organic carboxylic acids, amphoterics, phosphates, or borates.

5. An ophthalmic contact lens solution comprising: 0.001 to 10 percent by weight ethoxylated glyceride; 0.001 to 2 weight percent of a physiologically acceptable tonicity agent adjusted so the solution is isotonic between 240 and 310 mOsm/kg and 0.00001 to 0.1 weight percent of a polymeric preservative.

6. An ophthalmic solution comprising; 0.001 to 10 percent by weight ethoxylated glyceride; 0.00001 to 0.1 weight percent of a polymeric preservative agent.

7. A contact lens product comprising: a contact lens: a sealable container; and an ophthalmic lens solution comprising: 0.001 to 10 percent by weight ethoxylated glyceride; 0.01 to 2 weight percent of a physiologically acceptable buffer adjusted so the pH of solution is between 6.5 and 7.8, 0.00001 to 0.1 weight percent of a polymeric preservative and the balance water.

* * * * *